(12) United States Patent
Liu et al.

(10) Patent No.: US 8,934,100 B2
(45) Date of Patent: Jan. 13, 2015

(54) MULTI-BAND MULTIPLEXING INTRA-CAVITY GAS SENSING SYSTEM AND METHOD

(75) Inventors: Kun Liu, Tianjin (CN); Tiegen Liu, Tianjin (CN); Junfeng Jiang, Tianjin (CN); Xiao Liang, Tianjin (CN)

(73) Assignee: Tianjin University, Tianjin (CN)

( * ) Notice: Subject to any disclaimer, the term of this patent is extended or adjusted under 35 U.S.C. 154(b) by 0 days.

(21) Appl. No.: 13/880,731

(22) PCT Filed: Dec. 16, 2011

(86) PCT No.: PCT/CN2011/084105
§ 371 (c)(1),
(2), (4) Date: Apr. 20, 2013

(87) PCT Pub. No.: WO2013/023426
PCT Pub. Date: Feb. 21, 2013

(65) Prior Publication Data
US 2014/0176951 A1 Jun. 26, 2014

(30) Foreign Application Priority Data

Aug. 18, 2011 (CN) .......................... 2011 1 0237416

(51) Int. Cl.
*G01N 21/00* (2006.01)
*G01N 21/35* (2014.01)
*G01N 21/39* (2006.01)

(52) U.S. Cl.
CPC ............ *G01N 21/3504* (2013.01); *G01N 21/39* (2013.01); *G01N 2021/391* (2013.01)
USPC .......................................................... 356/437

(58) Field of Classification Search
CPC ..................................................... G02B 6/2938
USPC .................................................. 356/432, 437
See application file for complete search history.

(56) References Cited

U.S. PATENT DOCUMENTS 6,125,220 A * 9/2000 Copner et al. .................. 385/27
6,281,977 B1 * 8/2001 Paiam et al. .................. 356/480
(Continued)

FOREIGN PATENT DOCUMENTS

CN 100423385 C 5/2007
(Continued)

OTHER PUBLICATIONS

Jia, Dagong et al., Method of Gas Detection Based on Intra-Cavity Erbium-Doped Fiber Laser, Chinese Journal of Lasers, Sep. 2009, vol. 36, No. 9, pp. 2384-2387.
Lid, Kun et al., Investigation of Intra-Cavity Gas Sensing Technology Based on Wavelength Modulation, Chinese Journal of Lasers, Jan. 2011, vol. 38, No. 1, pp. 0105008-1 to 0105008-6.

*Primary Examiner* — Roy M Punnoose
(74) *Attorney, Agent, or Firm* — George G. Wang; Bei & Ocean

(57) ABSTRACT

Disclosed is a multi-band multiplexing intra-cavity gas sensing system and method. The system consists of a laser resonant cavity subsystem, a gas sensing subsystem and a detection-demodulation subsystem. The laser resonant cavity subsystem consists of the first beam splitter, two ways of gain paths composed of a pump light source, a wavelength division multiplexer, a rare earth doped fiber, an optical isolator and a tunable optical attenuator, a beam combiner and an F-P tunable optical filter. The gas sensing subsystem consists of a gas cell and an optical reflective mirror. The detection-demodulation subsystem consists of an optical coupler, the second beam splitter, two optical detectors, a data acquisition module and a computer. In this invention, different rare-earth doped fibers are multiplexing into one system, in order to cover more maser bands of different rare earth, which greatly expands the scanning range of wavelength, and is capable of detecting various gases simultaneously. New gain paths can be added to the system, to further expand the scanning range of wavelength. Hence, the present invention has strong expandability.

4 Claims, 6 Drawing Sheets

(56) References Cited

U.S. PATENT DOCUMENTS

| | | |
|---|---|---|
| 6,981,804 B2 * | 1/2006 | Jian .................................. 385/88 |
| 7,198,043 B1 | 4/2007 | Zhang |
| 7,764,379 B1 | 7/2010 | McDermott |
| 2010/0103426 A1 | 4/2010 | Kim et al. |

FOREIGN PATENT DOCUMENTS

| | | |
|---|---|---|
| CN | 100516836 C | 10/2007 |
| CN | 101762557 A | 6/2010 |
| JP | 10-246694 A | 9/1998 |
| WO | WO2007040528 A1 | 4/2007 |

* cited by examiner

MULTI-BAND MULTIPLEXING INTRA-CAVITY GAS SENSING SYSTEM AND METHOD

FIELD OF THE INVENTION

The present invention pertains to field of sensing and detecting technology.

BACKGROUND OF THE INVENTION

Online monitoring, indicating and controlling flammable, explosive, toxic and hazardous gases have been one of the important issues to be solved urgently for the high risk industries, such as coal mining, petroleum mining, chemistry and thermal power generation. In addition, a system to monitor and control toxic and hazardous gases is expected for maintaining a clean environment, with the improvement of living standards of human being. As a result, the development of a system for sensing and monitoring hazardous gases is essential and becomes a key topic in the field of sensing technology.

Gas detection method working with optical fiber sensing technique, especially near infrared absorption spectrum quantitative detection, has developed rapidly in the last two decades. As a novel optical fiber gas detection method provided in this invention, optical fiber active intra-cavity method is adopted. In this method, a gas cell is placed within a resonant cavity of an optical laser, and the wavelength of the laser varies with the absorption spectrum of the detected gas. During the process of laser generation by reciprocating resonance of weak optical signals inside the resonant cavity, the weak optical signals pass through the gas frequently, which leads to a fairly long effective optical path in the small gas cell. By this way, gas detection sensitivity is significantly improved. The system continuously scans the entire gain band of the laser. All the absorption spectrums of the gases inside the chamber are thus obtained. Hence, the system is capable of sensing different gases simultaneously.

In general, optical fiber containing rare earth is used as gain medium of an optical fiber laser. At present, the commonly used rare earth ions comprise $Nd^{3+}$, $Ho^{3+}$, $Er^{3+}$, $Tm^{3+}$, $Yb^{3+}$ and so on. Optical fiber doped with $Nd^{3+}$ has maser band at wavelength of 1.088 μm, optical fiber doped with $Ho^{3+}$ has maser band at wavelength of 2.1 μm, optical fiber doped with $Er^{3+}$ has high gain at wavelength of 1.55 μm, optical fiber doped with $Tm^{3+}$ has maser band at wavelength of 1.4 μm, and, optical fiber doped with $Yb^{3+}$ has relative wide excitation band at wavelength range of 0.97 μm-1.2 μm. The above statements indicate that the excitation band of optical fiber doped with rare earth covers almost entire near infrared bandwidth. However, the gain band of one optical fiber doped with rare earth elements covers only part of the bandwidth, with limited applicability in terms of gas types. To detect more gases, individual and separate optical fiber laser intra-cavity gas sensing systems with different bands should be applied.

This invention aims to provide a system capable of detecting more types of gases simultaneously, by expanding the scanning range of wavelength by combining the gain bands of a number of optical fibers doped with different rare earth materials.

SUMMARY OF THE INVENTION

The major object of the present invention is to provide a multi-band based multiplexing sensing system for intra-cavity gas in which plural active optical fibers doped with different rare earth ions are multiplexed in the same system such that the system covers gain band of various doped ions, hereby significantly extending wavelength scanning range of the system. The present invention resolves the problem of gain band of the rare-earth doped fiber only covering part of the entirety and can detect various types of gases.

The present invention bears strong expandability by inserting new gain path, thus further extending wavelength scanning range of the system.

The principles of the present invention are discussed as follows.

The present invention provides a multi-band based multiplexing sensing system for intra-cavity gas which greatly extends wavelength coverage of the gas sensed by the method of optical fiber active intra-cavity sensing. As such, the present system is able to detect and distinguish more types of gases.

Optical fibers doped with different rare earth ions such as $Nd^{3+}$, $Ho^{3+}$, $Er^{3+}$, $Tm^{3+}$, $Yb^{3+}$ have excitation bands of different wavelengths. In addition, different gas has different absorption wavelength. Gain band of more doping ions is covered at the same time, and output wavelength range of the laser is extended greatly, and capability of detecting more types of gases at one time is achieved, since active optical fibers doped with different rare earth ions are combined into one system.

As shown in FIG. 2, F-P tunable optical filter has comb transmission spectrum. Driven by linear voltage, the entire transmission spectrum is displaced toward the same direction. Furthermore, there is approximately linear relationship between the displacement and driving voltage. The free spectrum range of the F-P tunable optical filter (that is, interval between two adjacent transmission wavelengths) must be larger than the gain band of a doped optical fiber, and smaller than the interval of two gain bands of two adjacent different doped optical fibers. This ensures that within one free spectrum of the filter the transmission wavelength has definite relationship with the driving voltage. When the comb transmission spectrum of the F-P tunable optical filter is tuned continuously toward the same direction, the system continuously scans within respective gain bands of different doped optical fibers and output laser. Two optical detectors are used to obtain absorption spectrum curves of gases within respective gain bands. In other words, gas absorption spectrum curves gotten by the system within different gain bands are separated on the wavelength domain with the help of comb spectrum characteristics of the F-P tunable optical filter, thus facilitating detection and demodulation respectively.

Based on the above principles, the present invention offers a multi-band multiplexing sensing system and method for intra-cavity gas, as shown in FIG. 1. The sensing system includes a laser resonant cavity subsystem, a gas sensing subsystem and a detection-demodulation subsystem.

The first subsystem is a laser resonant cavity, consisting of the first beam splitter, pump light source, wavelength division multiplexer, doped optical fiber, optical isolator, and tunable optical attenuator. The first beam splitter having two output ports which are connected by the means of optical fiber with input ports of the first wavelength division multiplexer and the second wavelength division multiplexer, respectively. The other input ports of the first and second wavelength division multiplexers are coupled with output ports of the first pump light source and the second pump light source, respectively. The first wavelength division multiplexer is connected to the first doped optical fiber, the first optical isolator and the first tunable optical attenuator in turn, whereas the second wavelength division multiplexer is connected to the second doped optical fiber, the second optical isolator and the second tunable optical attenuator in turn. The output ports of the first and second optical attenuators are coupled with an input port of a beam combiner, respectively. The output port of the beam combiner is connected to the first port of an optical circulator, whereas the third port of the beam combiner is connected to the input port of the F-P tunable optical filter.

The pump light source, wavelength division multiplexer, doped optical fiber, optical isolator, and tunable optical attenuator constitute together gain path, which performs gain amplification to the optical signals inside the gain band of the input doped optical fiber. The optical isolator ensures single direction transmission of the amplified optical signals. The gain of the gain path can be changed by adjustment of output power of the pump light source or attenuation of the tunable optical attenuator. The wavelength band of the ports of the two beam splitters and beam combiner must be consistent with the gain band of the gain path corresponding to or connected with the ports, respectively.

The second subsystem is the gas sensing portion, consisting of a gas cell and an optical reflective mirror. The gas cell and optical reflective mirror are connected with the laser resonant cavity through the second port of the optical circulator. The optical reflective mirror reflects the signals output by the laser resonant cavity back to the same cavity so as to form laser resonance.

The third subsystem is detection-demodulation portion, consisting of an optical coupler and a computer. The input port is connected with the output port of the F-P tunable optical filter. An output port of the optical coupler is coupled with the input port of the second beam splitter. The two output ports of the second beam splitter are connected with the input ports of the first and second optical detectors respectively. The output ports of the first and second optical detectors are connected with an analog input port of a data acquisition module respectively. The data acquisition module is connected to a computer. The analog output port of the above module is connected with an electrically-controlled input port of the F-P tunable optical filter.

The two optical detectors detect the power of the laser signals output by corresponding gain band system.

The present invention has strong expandability, and the expanding method is described as follows. The port number of the first beam splitters and optical combiners is increased. A gain path, formed by the pump light source, optical division multiplexer, doped optical fiber, optical isolator and tunable optical attenuator, is added between the output port of the first beam splitter and input port of the optical combiner. At the same time, the number of the second beam splitters and analog input ports of the data acquisition module is also increased. A certain number of optical detectors are added between the output port of the second beam splitter and data acquisition module.

The gain band of the new gain path should meet three criteria as shown below: (1) it should be different from the gain band of the existed system gain path; (2) the gain band-width should be smaller than the free spectrum range of the F-P tunable optical filter; (3) the interval of it with the gain band of the existed system gain path should be larger than the free spectrum range of the F-P tunable optical filter. Furthermore, the system should also be provided with an optical detector for the detection of laser signals output by newly added gain path, said laser signals being acquired synchronously by the data acquisition module and processed by the computer after being input.

The present invention also provides a method for sensing gas type and concentration using the above system. The method includes the following steps.

At first, the first and second pump light sources are powered on and, the power of the two pump light sources is adjusted such that a sensing system outputs stable laser within the maser bands of the two doped optical fibers.

Secondly, mixed gases are introduced into the gas cell. The absorption spectrum of each type of gases inside the mixed gases should fall within the gain band of either the first doped optical fiber or the second doped optical fiber. The optical signals enter into the gas cell are reflected by the reflective mirror. Owing to single direction transmission feature of the circulator from its second port to the third port, the optical signals after absorption by the gas are output through the third port of the optical circulator.

Thirdly, the gas-absorbed optical signals within two wavebands pass through the optical coupler and are divided into two components by the second optical splitter and then are received by two optical detectors. The first and the second optical detectors are intended for absorbing signals of which the absorption spectrums are located in maser bands of the first and second doped optical fibers.

Fourthly, the analog output port of the data acquisition module outputs voltage waveform for driving the F-P tunable optical filter so as to realize transmission wavelength scanning. The two analog input ports acquire the optical voltage values output by the two optical detectors. All the analog output and input ports work synchronously.

Fifthly, two ways of gas-absorbed optical signals captured by the data acquisition module are transferred to the computer for further processing. Owing to correspondence between the transmission wavelength and driving voltage and based on value of the driving voltage, the absorption wavelength of the gas can be calculated. The absorption wavelength thus is calculated and compared with the optical spectrum database so as to determine gas type. According to Lambert-Beer Law, the concentration of the gas detected can be calculated using absorption of the gas absorption optical spectrum and optical intensity attenuation.

The present invention provides an intra-cavity gas sensing system in which several doped optical fibers with different gain wavebands are integrated into one system. The present system covers maser band of various kinds of ions within infrared optical spectrum. The system can distinguish and identify different gases and can also achieve gas concentration sensing. Compared with traditional intra-cavity laser gas sensing system comprising a singly doped optical fiber, the present system can detect more types of gases.

The above method can be used to distinguish and identify various gases and to perform concentration detection. It is applicable in mining industry, petroleum chemical industry, and environmental protection industry and so on, and has significant scientific value and economic benefits.

BRIEF DESCRIPTION OF THE DRAWINGS

FIG. 1 shows a schematic structural view of a multiple-band multiplexing intra-cavity gas sensing system according to the invention, in which:

1 represents a first beam splitter, 2 represents a first pump light source, 3 denotes a second pump light source, 4 denotes a first wavelength division multiplexer, 5 denotes a second wavelength division multiplexer, 6 denotes a first doped optical fiber, 7 denotes a second doped optical fiber, 8 is a first optical isolator, 9 is a second optical isolator, 10 is a first tunable optical attenuator, 11 is a second tunable optical attenuator, 12 is a beam combiner, 13 is an optical circulator, 14 is a gas cell, 15 is an optical reflective mirror, 16 is a F-P tunable optical filter, 17 is an optical coupler, 18 is a second beam splitter, 19 is a first optical detector, 20 is a second optical detector, 21 is a data acquisition module, and 22 is a computer.

Figure 2:
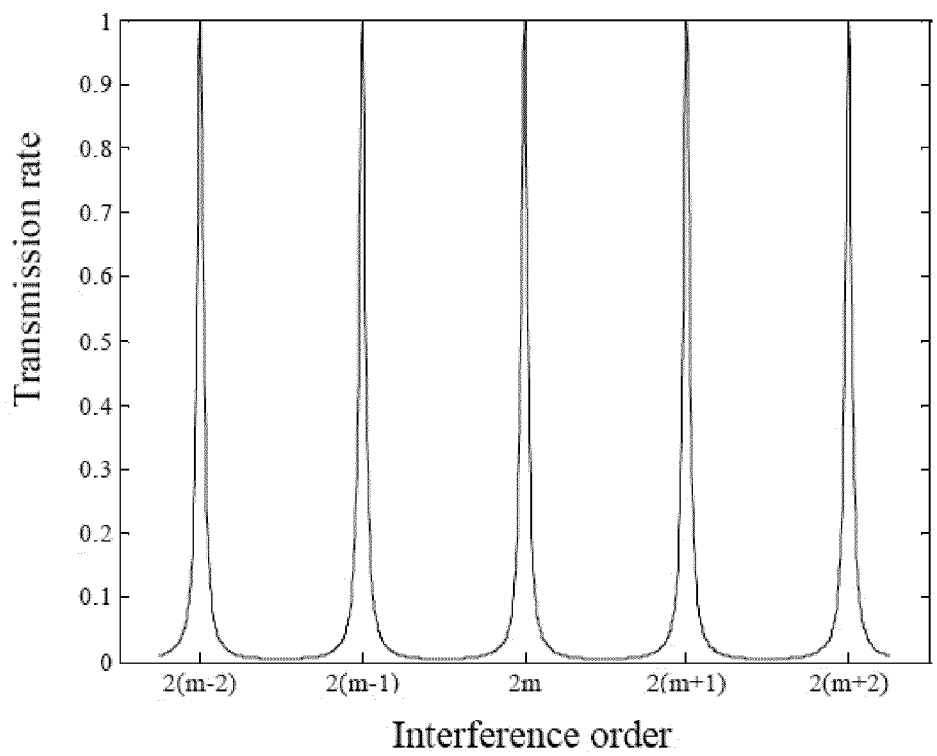
Figure 3:
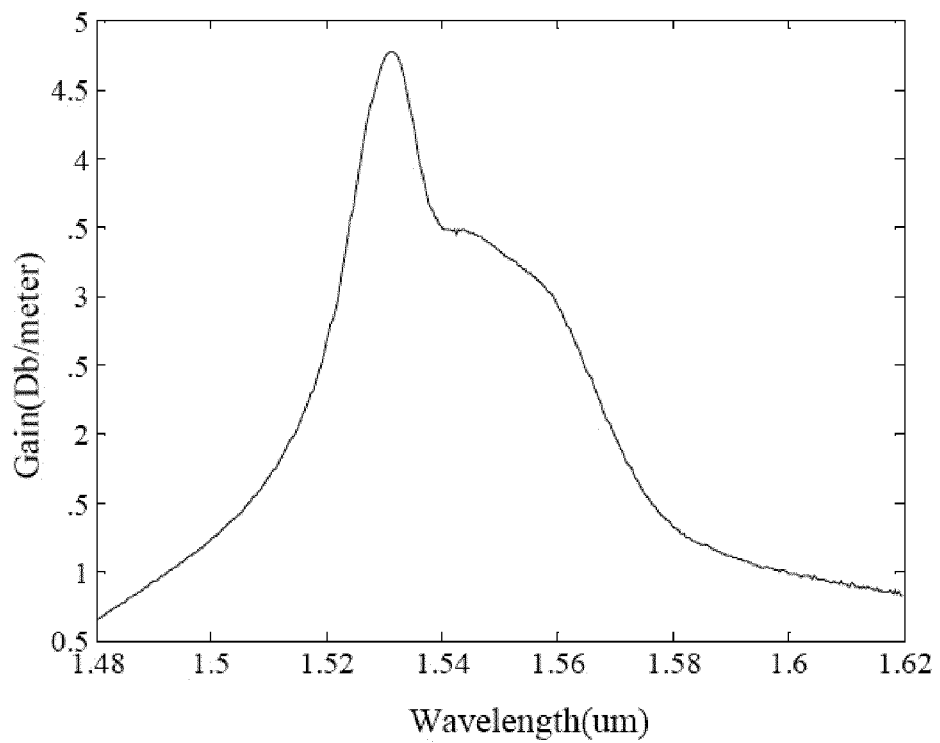
Figure 4:
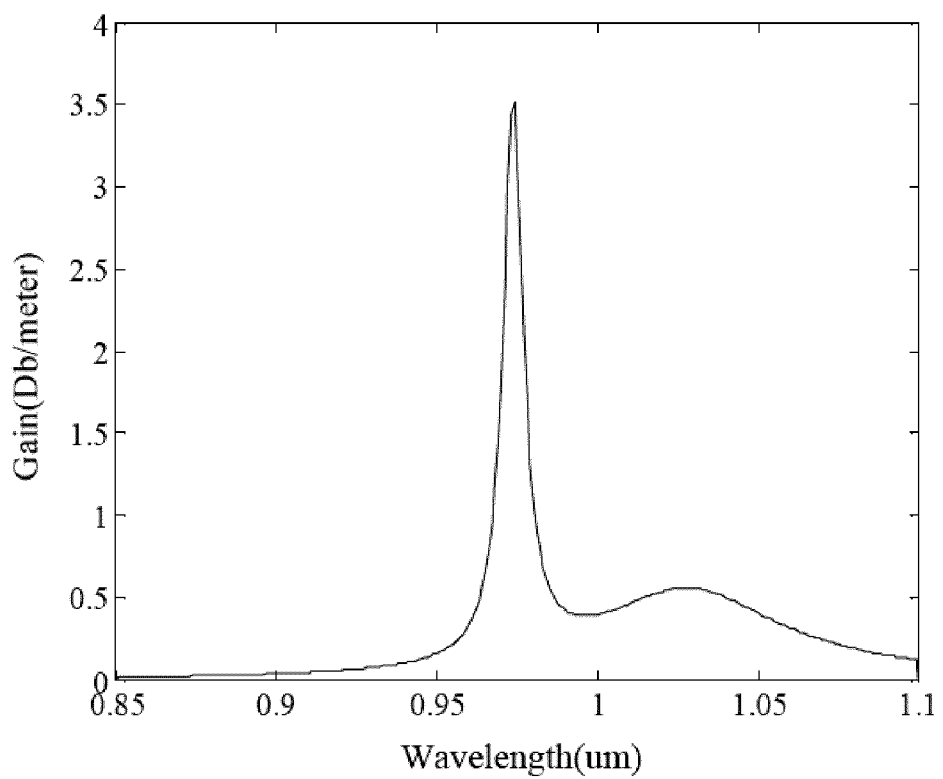
Figure 5:
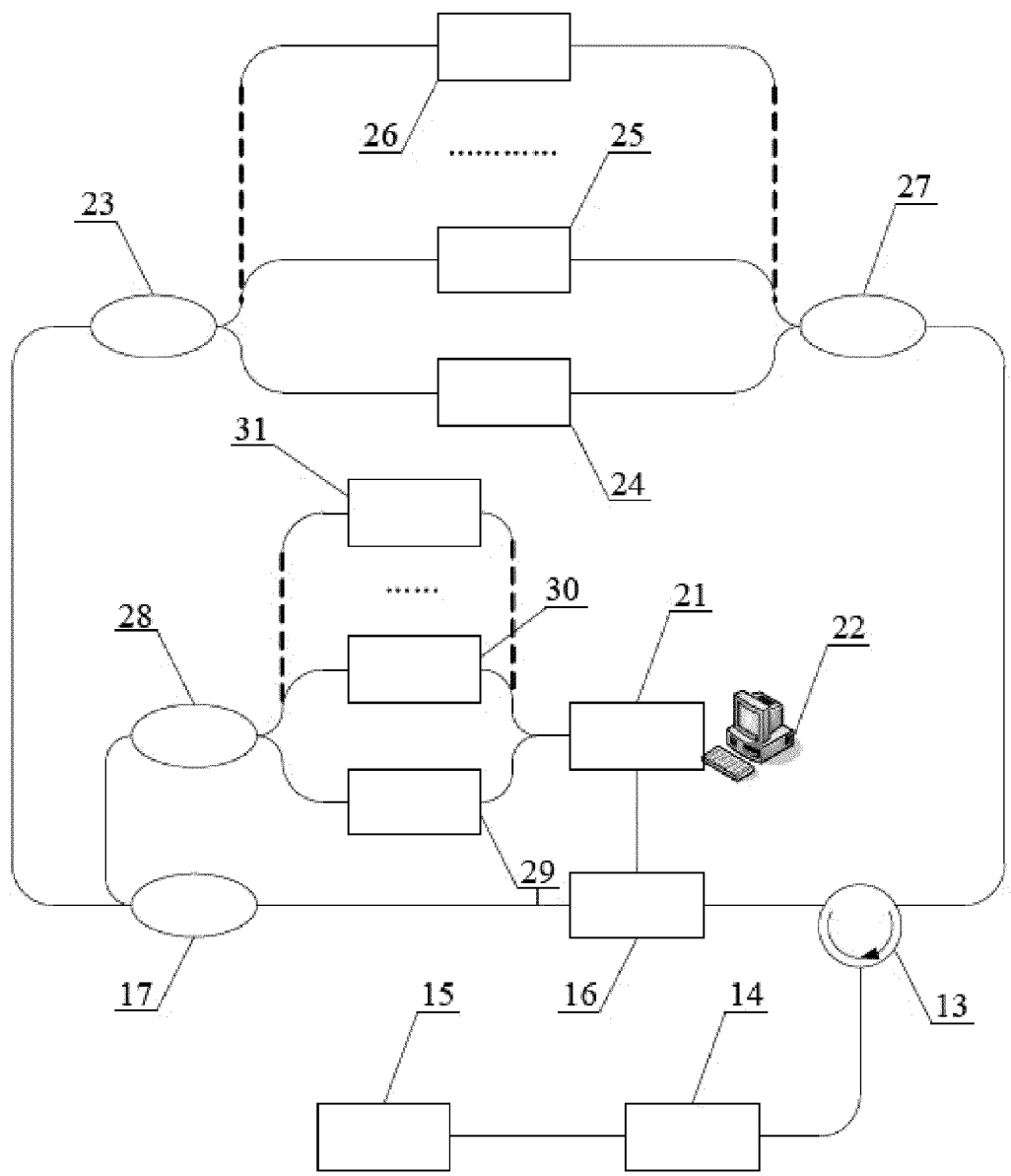

FIG. 2 shows comb transmission spectrum of the F-P tunable optical filter;

FIG. 3 shows gain spectrum of an optical fiber doped with erbium;

FIG. 4 shows gain spectrum of an optical fiber doped with ytterbium;

FIG. 5 shows an expanded view of a multiple-band multiplexing intra-cavity gas sensing system, in which:

23 denotes the first N beam splitter, 24 denotes the first gain path, 25 denotes the second gain path, 26 is the Nth gain path, 27 is N beam combiner, 13 is an optical circulator, 14 is a gas cell, 15 is an optical reflective mirror, 16 is the F-P tunable optical filter, 17 is an optical coupler, 28 is a second N beam splitter, 29 is a first optical detector, 30 is a second optical detector, 31 is the Nth optical detector, 21 is the data acquisition module, while 22 is the computer.

Figure 6:
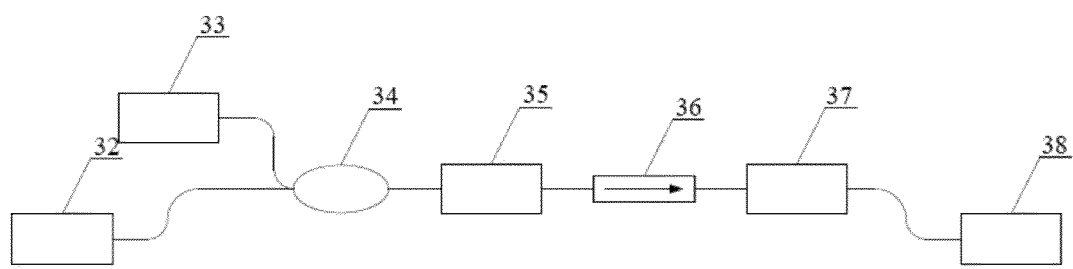

FIG. 6 shows a constructional view of a gain path, in which:

32 represents optical signal input port, 33 is a pump light source, 34 is wavelength division multiplexer, 35 is an rare-earth doped fiber, 36 is an optical isolator, 37 is a tunable optical attenuator, and 38 is optical signal output port.

DETAILED DESCRIPTION OF PARTICULAR EMBODIMENTS OF THE INVENTION

Figure 1:
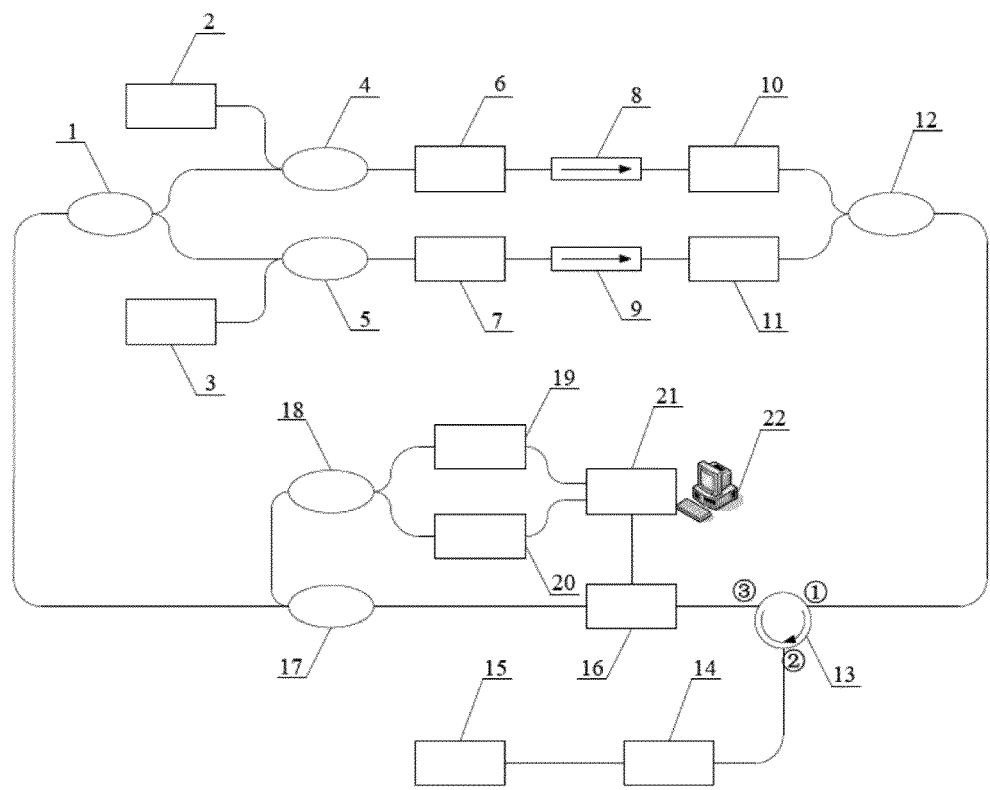

Embodiment 1: Preferable Technical Scheme for a Multi-Band Multiplexing Intra-Cavity Gas Sensing System The embodiment of the multiple-band multiplexing intra-cavity gas sensing system is described with examples of optical fibers doped with erbium and ytterbium, respectively. The schematic construction of the system is illustrated in FIG. 1. The system consists of a beam splitter, a pump light source, a wavelength division multiplexer, two optical fibers (the optical fibers doped with erbium and ytterbium respectively), an optical isolator, a tunable optical attenuator, a beam combiner, an optical circulator, a gas cell, an optical reflective mirror, a F-P tunable optical filter, an optical coupler, an optical detector, a data acquisition module and a computer.

A gain path 1 is constructed by the first pump light source with a wavelength of 980 nm, the first wavelength division multiplexer 4 (980 nm/1550 nm), an optical fiber doped with erbium 6, the first optical isolator 8 (1550 nm), and the first tunable optical attenuator 10 (1550 nm). A gain path 2 is constructed by the second pump light source 3 with a wavelength of 980 nm, the second wavelength division multiplexer 5 (980 nm/1050 nm), an optical fiber doped with ytterbium 7, the second optical isolator 9 (1050 nm), and the second tunable optical attenuator 11 (1050 nm). The optical isolators 8 and 9 are used to keep optical signals transmitting along a single direction on corresponding gain paths. The gain of the gain path 1 can be adjusted by changing the output power of the pump light source 2 or attenuation of the tunable optical attenuator 10. The gain of the gain path 2 can be adjusted by changing the output power of the pump light source 3 or attenuation of the tunable optical attenuator 11. The wavelength ranges of respective ports of the beam splitters 1 and 18 and beam combiner 12 are 1.48-1.62 µm and 0.95-1.1 µm, which correspond to the gain bands of the optical fibers doped with erbium and ytterbium respectively. The port of which the wavelength ranges from 1.48 µm to 1.62 µm is connected with the gain path 1, while the port of which the wavelength ranges from 0.95 µm to 1.1 µm is connected with the gain path 2. The optical detector 19 functions to detect the laser signals generated in wavelength range of 1.48 µm to 1.62 µm by the gain path 1, while the optical detector 20 functions to detect the laser signals generated in wavelength range of 0.95 µm to 1.1 µm by the gain path 2. Other optical components of the system have a general wavelength range of 1.48 µm to 1.62 µm and 0.95 µm to 1.1 µm.

As shown in FIG. 2, the F-P tunable optical filter has comb spectrum. Driven by the driving voltage, its transmission spectrum can perform continuous scanning within certain wavelength range. The transmission wavelength value of the F-P tunable optical filter determines the wavelength of the laser output by the system. To ensure the certainty and uniqueness of the wavelength of the laser output, the system is maintained within the same gain band all the time. The free optical spectrum of the F-P tunable optical filter (namely, the interval of two adjacent transmission wavelengths) should be larger than the gain bandwidth of the optical fibers doped with erbium and ytterbium respectively, and smaller than the interval of the bandwidths between the two. As shown in FIG. 3, the gain spectrum of the optical fiber doped with erbium is illustrated, whereas that of the optical fiber doped with ytterbium is illustrated in FIG. 4. Resultantly, the free optical spectrum of the F-P tunable optical filter should be no less than 200 nm. Meanwhile, to maintain accuracy of the gas absorption spectrum, the precision of the F-P tunable optical filter should be no less than 5000.

In the system, a laser resonant cavity is constituted by interconnection among the first beam splitter 1, two gain paths, a beam combiner 12, an optical circulator 13, an F-P tunable optical filter 16 and an optical coupler 17 through optical fiber. The gas cell 14 and optical reflective mirror 15 are connected with the laser resonant cavity via the optical circulator 13. The optical reflective mirror 15 reflects the signals output by the cavity back to the cavity by means of the gas cell 14 so as to form laser resonance.

In fact, the present system is equivalent to an aliasing construction formed by erbium-doped optical fiber intra-cavity gas sensing system and ytterbium-doped optical fiber intra-cavity gas sensing system. A complete systematic construction and two gain paths are employed to obtain all the functions of the two complete systems, thus obtaining better systematic integrity and generality.

Embodiment 2: Preferable Technical Scheme for Demodulation of a Multiple-Band Aliasing Intra-Cavity Gas Sensing System The embodiment of the demodulation of a multiple-band aliasing intra-cavity gas sensing system will be described with examples of a multiple-band aliasing intra-cavity gas sensing system of the optical fibers doped with erbium and ytterbium respectively. As shown in FIG. 1, a systematic construction is illustrated. The voltage waveform output by the analog output port of the data acquisition module connected with the computer is used for driving the F-P tunable optical filter so as to achieve scanning of transmission wavelength. The two analog input ports are intended to capture optical voltage value output by the two ways of optical detectors. All the analog input and output ports work at the same time, thus making sure that there is definite correspondence between the wavelength of laser output by the system and optical power value.

Driven by linear voltage, the entire comb transmission spectrum is displaced toward the same direction. Furthermore, there is an approximately linear relationship between the displacement and driving voltage. When the comb transmission spectrum of the F-P tunable optical filter is tuned continuously toward the same direction, the system performs continuous scanning within respective gain bands of the optical fibers doped with erbium and ytterbium respectively and output laser. Two optical detectors 19 and 20 are used to obtain full absorption spectrum curves of all the gas inside the gas cell within band range of 1.48-1.62 μm and 0.95-1.1 μm. In the other words, full absorption spectrum within the gain bands of the optical fibers doped with erbium and ytterbium respectively scanned synchronously by the system is separated on the wavelength domain with the help of comb spectrum characteristics of the F-P tunable optical filter, thus facilitating detection and demodulation respectively.

When there is no gas to be detected inside the gas cell, the actual light intensity captured by the system is $I_0(\lambda)$, where $\lambda \in [0.95 \ \mu m, 1.1 \ \mu m] \cup [1.48 \ \mu m, 1.62 \ \mu m]$. When gas to be detected is present in the gas cell, the actual light intensity obtained by the system is $I(\lambda)$, where $\lambda \in [0.95 \ \mu m, 1.1 \ \mu m] \cup [1.48 \ \mu m, 1.62 \ \mu m]$. In this case, the absorbance of the gas $K(\lambda) = \ln[I_0(\lambda)/I(\lambda)]$, where $\lambda \in [0.95 \ \mu m, 1.1 \ \mu m] \cup [1.48 \ \mu m, 1.62 \ \mu m]$. In the gain band of the optical fibers doped with erbium and ytterbium respectively, the transmission wavelength of the F-P tunable optical filter is determined definitely by its driving voltage. That is:

$$\begin{cases} \lambda_i = V(V_i), \lambda_i \in [0.95 \ \mu m, 1.1 \ \mu m] \\ \lambda_j = V(V_j), \lambda_j \in [1.48 \ \mu m, 1.62 \ \mu m] \end{cases} \quad (1)$$

Wherein $V_i$ and $V_j$ represent driving voltage value of the F-P tunable optical filter. As such, within the gain band of the same rare-earth doped fiber, the gas absorbance is the definite and sole function $K(V_i)$ of the driving voltage of the F-P tunable optical filter. Within a different gain band, the relationship between transmission wavelength of the F-P tunable optical filter and its driving voltage can be determined by calibration in advance. The gas absorbance curve $K(V_i)$ is searched for the driving voltage at absorption peak and, with the help of expression (1), wavelength value of the gas absorption can be calculated. Under the assistance of the optical spectrum database, the gas type can be determined. Some gas types and absorption wavelengths covered by the gain band of the optical fiber doped with erbium are listed in table 1, and some gas types and absorption wavelengths covered by the gain band of the optical fiber doped with ytterbium are listed in table 2. It is clear from tables 1 and 2 that, multiplexing intra-cavity gas sensing system based optical fibers doped with erbium and ytterbium respectively can detect more types of gas.

According to Lambert-Beer Law, the gas absorbance can also be expressed as $K(\lambda) = \alpha(\lambda)cL$, wherein $\alpha(\lambda)$ is absorptive section of the gas relative to beam, c is concentration of the gas, and L is effective absorption optical path. Therefore, there is linear relationship between the concentration of the gas and light intensity loss resulted by absorption of the gas absorption spectrum. If the concentration-absorbance curve is calibrated in advance, the concentration of the gas can be calculated according to the peak value of the absorbance. Accordingly, the present system can realize detection of various types of gas and detection of concentration.

Table 1. Gas Type and Absorption Wavelength Covered by Gain Band of Optical Fiber Doped with Erbium

| Gas type | Peak wavelength of gas absorption (nm) |
|---|---|
| $C_2H_2$ | 1530 |
| $NH_3$ | 1544 |
| CO | 1567 |
| $CO_2$ | 1573 |
| $H_2S$ | 1578 |

Table 2. Gas Type and Absorption Wavelength Covered by Gain Band of Optical Fiber Doped with Ytterbium

| Gas type | Peak wavelength of gas absorption (nm) |
|---|---|
| HBr | 1026 |
| $CO_2$ | 1049 |
| $O_2$ | 1068 |
| $H_2O$ | 1092 |
| NO | 1095 |
| $CH_4$ | 1098 |

Embodiment 3: Preferable Technical Scheme for Expandability of a Multiple-band Aliasing Intra-cavity Gas Sensing System The present system has strong expandability as shown in FIG. 5. The construction of the gain path is illustrated in FIG. 6. A number of new gain paths can be added by increasing number of the beam splitter and ports of the beam combiner. The gain band of the new gain path should meet three conditions as shown below: (1) it should be different mutually from the gain band of the existed system gain path; (2) the gain bandwidth should be smaller than the free spectrum range of the F-P tunable optical filter; (3) the interval of it with the gain band of the existed system gain path should be larger than the free spectrum range of the F-P tunable optical filter. Further, the system should also be provided with an optical detector for detection of laser signals output by newly added gain path, said laser signals being acquired synchronously by the data acquisition module and processed by the computer after being input. The expanded system is equivalent to combination of several single rare-earth doped fiber intra-cavity gas sensing systems, thus resulting in wider gain band coverage and stronger gas detection ability.

What is claimed is:

1. An intra-cavity gas sensing system based on a multi-band aliasing construction, comprising a laser resonant cavity subsystem, a gas sensing subsystem and a detection-demodulation subsystem, wherein said laser resonant cavity subsystem is a laser resonant cavity and comprises a first beam splitter with two output ports, a first and a second wavelength division multiplexes each with a first input port and a second input port, a first and a second pump light sources each with an output port, a first and a second doped optical fibers, a first and second optical isolators, a first and a second tunable optical attenuators each with an output port, a beam combiner with an input port and an output port, an optical circulator with a first, a second and a third ports and an F-P tunable optical filter with an first and a second input ports, said two output ports of said first beam splitter being connected with said first input ports of said first and second wavelength division multiplexes respectively, said second input ports of said first and second wavelength division multiplexes being connected with said output ports of said first and second pump light sources respectively, said first wavelength division multiplexor being connected to the said first doped optical fiber, said first optical isolator and said first tunable optical attenuator in turn, said second wavelength division multiplexor being connected to said second doped optical fiber, said second optical isolator and said second tunable optical attenuator in turn, said output ports of said first and second tunable optical attenuators being coupled with said input port of said beam combiner, said output port of said beam combiner being connected to said first port of said optical circulator, and said third port of said optical circulator being connected to said first input port of said F-P tunable optical filter;

said gas sensing subsystem comprises a gas cell and an optical reflective mirror, said gas cell and optical reflective mirror being connected with said laser resonant cavity via said second port of said optical circulator and said optical reflective mirror reflecting signals output by said laser resonant cavity back to said same cavity to realize laser resonance; and said detection-demodulation subsystem comprises an optical coupler with an input port and an output port, a second beam splitter with an input port and two output ports, a first and a second optical detectors each with an input port and an output port, and a data acquisition module connected to a computer, said input port of said optical coupler being connected with said output port of said F-P tunable optical filter, said output port of said optical coupler being coupled with said input port of said second beam splitter, said two output ports of said second beam splitter being connected with said input ports of said first and second optical detectors respectively, said output ports of said first and second optical detector being connected with two analog input ports of said acquisition module respectively, and said data acquisition module having an analog output port connected with said second input port of said F-P tunable optical filter.

2. The intra-cavity gas sensing system of claim 1, wherein said first beam splitter has an N number of output ports and said beam combiner has an N number of input ports to form an N number of gain paths between said first beam splitter and said beam combiner, each comprising a pump light source, optical division multiplexor, doped optical fiber, optical isolator and tunable optical attenuator, said N being greater than two.

3. The intra-cavity gas sensing system of claim 2, wherein said second beam splitter has an N number of output ports and said data acquisition module has an N number of analog input ports to form an N number of paths between said second beam splitter and said data acquisition module, each comprising an optical detector.

4. A method for sensing the type and concentration of a gas using the of claim 1, comprising steps:

(a) powering on said first and second pump light sources and adjusting operating power of said two pump light sources so that said system outputs a stable laser within the maser band of said two doped optical fibers;

(b) introducing a mixture of gases into said gas cell, wherein each gas in said mixture has an absorption spectrum within the maser band of either said first or said second doped optical fiber, and optical signals entering into said gas cell are subjected to gas absorption, reflected by said reflective mirror and outputted through said third port of said optical circulator owing to a feature that provides a single direction transmission from said second port to said third port of said optical circulator;

(c) passing said outputted optical signals of step(b) through said optical coupler and then said second optical splitter, with said outputted optical signals being divided into two components received by said two optical detectors, which are intended for absorbing signals having absorption spectrums located in said first and second doped optical fibers' master bands, respectively;

(d) realizing transmission wavelength scanning by having said data acquisition module output a voltage waveform to drive said F-P tunable optical filter, wherein two analog input ports of said data acquisition module acquire optical voltage value outputs from said two optical detectors respectively and said analog output and input ports of said data acquisition module work synchronously; and (e) transferring signals captured by said data acquisition module to said computer for calculating an absorption wavelength of a gas, determining the type of said gas by searching in a database of optical spectrum for gases in comparison with said absorption wavelength of said gas, and determining the concentration of said gas according to the Lambert-Beer Law.

* * * * *